(12) United States Patent
Shi et al.

(10) Patent No.: US 11,274,078 B2
(45) Date of Patent: Mar. 15, 2022

(54) DRUG FOR TREATING TUMOR DISEASES AND HAVING ANTIBACTERIAL ANTIVIRUS ANTI-INFLAMMATORY EFFECTS

(71) Applicants: Jianyou Shi, Chengdu (CN); Baowen Qi, Montreal (CA)

(72) Inventors: Jianyou Shi, Chengdu (CN); Baowen Qi, Montreal (CA)

(*) Notice: Subject to any disclaimer, the term of this patent is extended or adjusted under 35 U.S.C. 154(b) by 108 days.

(21) Appl. No.: 16/603,714

(22) PCT Filed: Apr. 10, 2017

(86) PCT No.: PCT/CN2017/079856
§ 371 (c)(1),
(2) Date: Oct. 8, 2019

(87) PCT Pub. No.: WO2018/187894
PCT Pub. Date: Oct. 18, 2018

(65) Prior Publication Data
US 2021/0094910 A1    Apr. 1, 2021

(51) Int. Cl.
| *C07C 311/46* | (2006.01) |
|---|---|
| *C07C 237/48* | (2006.01) |
| *C07D 213/61* | (2006.01) |
| *C07D 295/033* | (2006.01) |

(52) U.S. Cl.
CPC .......... *C07C 311/46* (2013.01); *C07C 237/48* (2013.01); *C07D 213/61* (2013.01); *C07D 295/033* (2013.01)

(58) Field of Classification Search
None
See application file for complete search history.

*Primary Examiner* — Craig D Ricci

(57) ABSTRACT

The present disclosure describes an anti-cancer drug for treating tumor diseases and providing antibacterial, antivirus, and anti-inflammatory effects. The drug contains a naphthalene dicarboxamide compound with a structural formula as shown in Formula I or a biologically acceptable salt or ester form of the compound with the formula I as an active ingredient. The drug is able to help inhibit the growth of tumor cells and possesses certain antibacterial, antivirus, and anti-inflammatory effects.

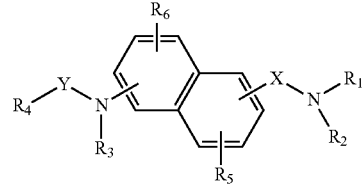

Formula I

6 Claims, 2 Drawing Sheets

DRUG FOR TREATING TUMOR DISEASES AND HAVING ANTIBACTERIAL ANTIVIRUS ANTI-INFLAMMATORY EFFECTS

FIELD

The present disclosure is in the field of biomedicine, chemistry, medicine, microbiology, and drug production, especially for tumor and cancer treatment.

BACKGROUND

With the fast pace of modern society and high pressure in daily work, many people are suffering in a suboptimal health status (SHS). An insufficiency of autoimmunity leads to increasing incidences of various diseases, which seriously threaten people's lives. Since the 20th century, organic chemical synthesis has played a vital role for novel small molecules discoveries to treat various diseases due to their unique spatial stereo structure, electronic distribution, and spatial arrangement of active groups.

Naphthalene diamides are based on naphthalene rings as a parent nucleus, connecting with two amide bonds. It can interact electrically with enzymes and receptors related to cancer in organisms through the interaction of amides and electron-rich groups. Meanwhile, aromatic rings in the structure can stack with enzymes and receptors to inhibit the occurrence of cancer.

SUMMARY

The present disclosure describes a naphthalene diamide compound comprising a structure expressed by the following structural formula, a synthesis method of preparing the compound, and in vitro anti-tumor cell activity screening studies.

In another aspect, the present disclosure describes a pharmaceutical compound or composition for treatment of cancer and a drug containing the naphthalene dicarboxamide compound with the structural formula as shown below or a biologically acceptable salt or ester with said compound as an active ingredient. The anti-cancer drug is able to inhibit the growth of tumor cells and has certain antibacterial, antiviral, and anti-inflammatory effects.

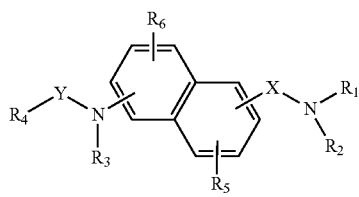

DETAILED DESCRIPTION

Figure 1:
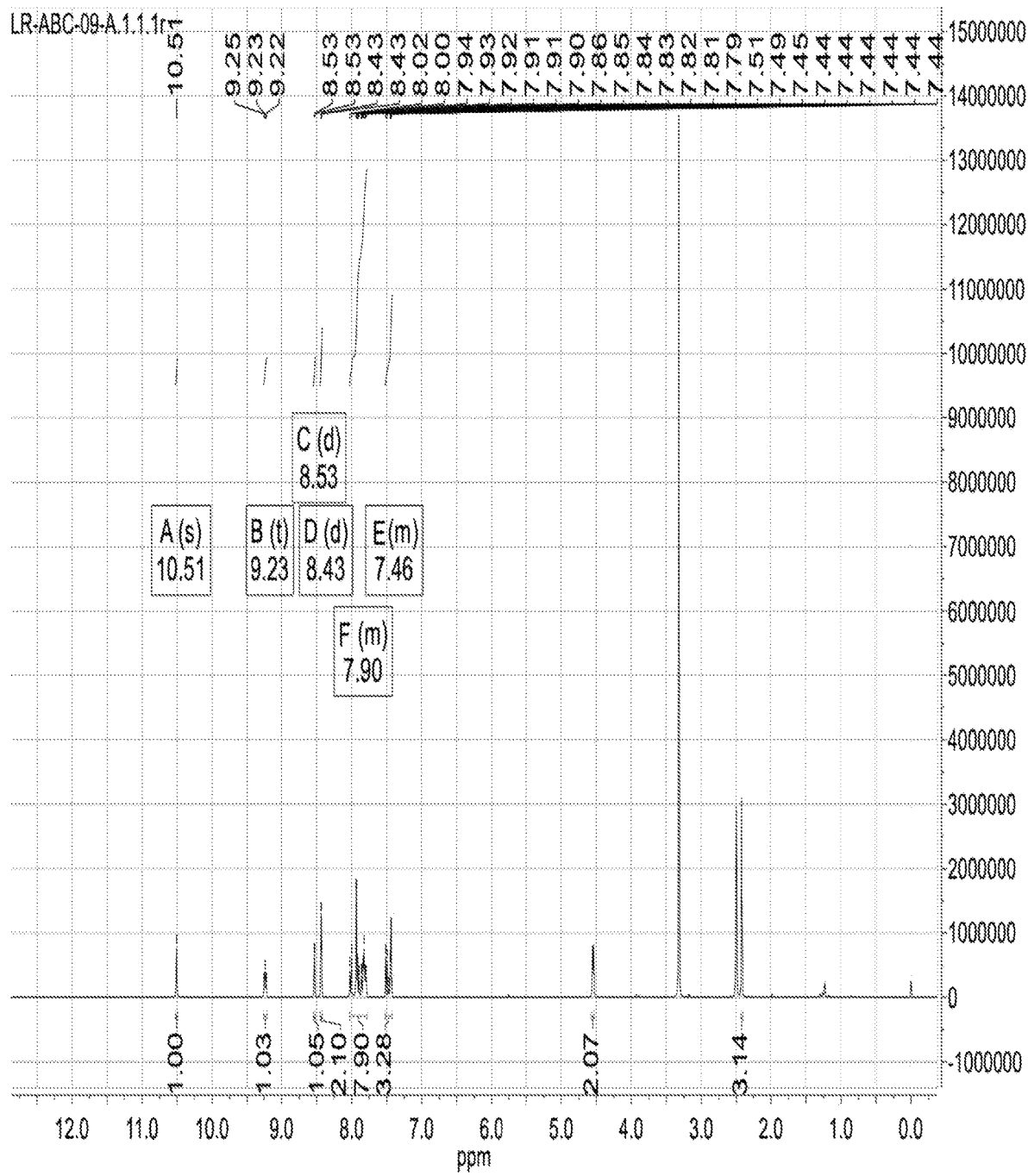
FIG. 1 illustrates an ABC-09 nuclear magnetic resonance spectrum of the compound and/or drug of the present disclosure.

The terminology used herein is for the purpose of describing particular embodiments only and is not intended to be limiting of the disclosure. As used herein, the term "and/or" includes any and all combinations of one or more of the associated listed items. As used herein, the singular forms "a," "an," and "the" are intended to include the plural forms as well as the singular forms, unless the context clearly indicates otherwise. "they", "he/she", or "he or she" or are used interchangeably because "they", "them", or "their" can now be used as singular gender-neutral pronoun in modern English. It will be further understood that the terms "comprises" and/or "comprising" when used in this specification, specify the presence of stated features, steps, operations, elements, and/or components, but do not preclude the presence or addition of one or more other features, steps, operations, elements, components, and/or groups thereof. Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein. In the description, it will be understood that a number of techniques and steps are disclosed. Each of these has an individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the disclosure and the claims.

In the following description, for purposes of explanation, numerous specific details are set forth to provide a thorough understanding of the present disclosure. It will be evident, however, to one ordinarily skilled in the art that the present disclosure may be practiced without these specific details. The present disclosure is to be considered as an exemplification of the disclosure and is not intended to limit the disclosure to the specific embodiments illustrated by the figures or description below. The present disclosure will now be described by referencing the appended figures representing preferred or alternative embodiments.

Some of the technical terms in the present disclosure are explained as follows: Lower alkyl groups include, but are not limited to, methyl, ethyl, propyl, isopropyl, cyclopropyl, butyl, isobutyl, tert-butyl, N-pentyl, isoamyl, neopentyl, heji, heptyl. Halogens include fluorine, chlorinated, brominated, and iodine. $C_{1-12}$ alkyl includes, but is not limited to, methyl, ethyl, propyl, isopropyl, butyl, isobutyl, tert-butyl, n-pentyl, isopentyl, neopentyl, sec-pentyl, tert-amyl, hexyl, heptyl, octyl, nonyl, decyl. $C_{1-7}$ alkyl includes, but is not limited to, methyl, ethyl, propyl, Isopropyl, butyl, isobutyl, tert-butyl, n-pentyl, isopentyl, neopentyl, sec-pentyl, tert-amyl base, hexyl, heptyl, etc. Lower alkenyl groups include, but are not limited to, vinyl, propylene, butenyl, pentenyl, hexenyl, heptenyl, hepene, octenyl. $C_{3-7}$ cycloalkyl groups include, but are not limited to, cyclopropyl, cyclobutyl, cyclopentyl, cyclohexyl, cycloheptyl.

The present disclosure provides a naphthalene diamide compound with a structure expressed by Formula I, a synthesis method of preparing the compound, and in vitro anti-tumor cell activity screening studies.

In another aspect, the present disclosure describes a pharmaceutical compound or composition for treatment of cancer and a drug containing a naphthalene dicarboxamide compound with a structural formula as shown below or a biologically acceptable salt or ester with said compound as an active ingredient. To achieve the above goals, the present disclosure provides the following technical solutions: a naphthalene diamide based chemical structure as shown in Formula I,

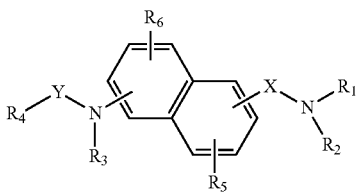

Formula I where X and Y can be separately selected from carbonyl, thiocarbonyl, and sulfonyl groups. $R_1$, $R_2$ together with adjacent nitrogen atoms can form a ring of 3 to 12 atoms or a ring structure substituted by a substituent M.

Alternatively, $R_1$ and $R_2$ can be independently selected from hydrogen, $C_{1-12}$ alkyl, $C_{1-12}$ alkoxy, $C_{3-7}$ cycloalkyl, $C_{1-12}$ alkoxycarbonyl, $C_{1-12}$ alkylcarbonyl, aminocarbonyl, $C_{1-12}$ alkylaminocarbonyl, nitro, oxazoly, thiazoly, pyridyl, pyridine, dihydropyridyl, tetrahydropyridyl, piperidinyl, thiazinyl, pyrrolyl, imidazolyl, pyrazolyl, pyrimidinyl, piperaziny, morpholinyl, furanyl, pyranyl, and other heterocyclic groups. They can also be independently selected from the above-mentioned groups, aryl groups, benzyl groups, aryl hydrocarbon group, and heteroaryl hydrocarbon group, which are selectively replaced by substituted group M. When $R_1$ and $R_2$ are replaced by substituent M, the number of substituent M can be single or multiple. If the substituents M are multiple, they are not relevant to each other, or they form a ring structure. If two substituents M form a ring structure and the linked group substituted by substituent M is also a ring structure, they may or may not form a heterocyclic ring structure.

Substitute M can be hydrogen, fluorine, chlorine, bromine, iodine, cyano, nitro, hydroxyl, amino, $C_{1-12}$ alkyl, halogenated $C_{1-12}$ alkyl, perfluoro-$C_{1-12}$ alkyl, polyhalogenated $C_{1-6}$ alkyl, aryl, substituted aryl, $C_{1-12}$ alkylamino, $C_{3-12}$ cycloalkylamino, di($C_{1-12}$ alkyl)amino, $C_{3-12}$ cycloalkyl, and substituted $C_{3-12}$ cycloalkyl.

The aryl hydrocarbon group substituted by the substituent M is a halogenated halophenyl hydrocarbon, alkoxyalkyl, perfluoroalkylphenyl hydrocarbon, hydrocarbyl-substituted phenyl hydrocarbon, nitro-substituted phenyl hydrocarbon, or hydroxyl-substituted phenylhydrocarbyl.

The heteroaryl hydrocarbon group substituted by substituent M includes halogenated pyridine hydrocarbon group, halogenated furan hydrocarbon group, halogenated thiazolidine, halogenated pyrimidine hydrocarbyl, halogenated imidazolium, nitro-substituted pyridine hydrocarbon, nitro-substituted furanyl, nitro-substituted thiazolidine, nitro-substituted pyrimidine hydrocarbyl, nitro-substituted imidazolium, amino-substituted pyridine hydrocarbon group, amino-substituted furan hydrocarbyl, amino substituted thiazolyl, amino substituted pyrimidine hydrocarbyl, and amino substituted imidazolium.

$R_3$ can be selected from hydrogen, fluorine, chlorine, bromine, iodine, nitro, amino, $C_{1-3}$ alkyl, $C_{1-3}$ alkoxy, $C_{3-7}$ cycloalkyl, halogen substituted $C_{3-7}$ cycloalkyl, halogenated $C_{1-12}$ alkyl, $C_{2-12}$ alkenyl, hydroxyl-substituted $C_{1-12}$ alkyl, $C_{1-12}$ alkoxy, $C_{1-12}$ alkoxycarbonyl, aminocarbonyl, $C_{1-6}$ alkylaminocarbonyl, Di($C_{1-12}$ alkyl)aminocarbonyl, $C_{3-7}$ cycloalkylaminocarbonyl, $C_{3-7}$ cycloalkoxy, hydroxy-$C_{1-12}$ alkoxy, halogenated $C_{1-12}$ alkoxy, amino $C_{1-12}$ alkyl, amino $C_{1-12}$ alkoxy, $C_{1-12}$ alkyl sulfone, $C_{2-12}$ alkenyl sulfone, $C_{3-7}$ cycloalkyl sulfone, heterocyclic oxy, amino-substituted piperidinyl, N-methylpiperidin-4-carbonyl, piperazine-$C_{1-12}$ alkyl, formamide, and N-methyl piperidine carboxamide.

$R_4$ can be selected from hydrogen, $C_{1-12}$ alkyl, $C_{1-12}$ alkoxy, $C_{3-7}$ cycloalkyl, halogen substituted $C_{3-7}$ cycloalkyl, $C_{1-6}$ alkoxycarbonyl, $C_{1-12}$ alkylcarbonyl, aminocarbonyl, $C_{1-12}$ alkylaminocarbonyl, nitro, amino, $C_{1-3}$ alkyl substituted amino, Di($C_{1-3}$ alkyl) substituted amino, oxazolyl, thiazolyl, pyridyl, dihydropyridyl, tetrahydropyridyl, piperidinyl, thiazinyl, pyrrolyl, imidazolyl, pyrazolyl, pyrimidinyl, piperazinyl, morpholinyl, furanyl, pyranyl, and other heterocyclic groups. The following groups can optionally be substituted by a substituent Q: an aryl group, a benzyl group, a heteroaryl group, an arylalkyl group, and a heteroaryl hydrocarbon group. The substituent Q can be double and multiple groups independently, which form ring structures via molecular interconnections.

When each substituent Q is an independent substituent, each substituent Q can be separately selected from hydrogen, fluorine, chlorine, bromine, iodine, cyano, nitro, hydroxyl, amino, $C_{1-12}$ alkyl, halogenated $C_{1-12}$ alkyl, perfluoro-$C_{1-12}$ alkyl, polyhalogenated $C_{1-12}$ alkyl, $C_{1-12}$ alkoxy, halogenated $C_{1-12}$ alkoxy, aryl, substituted aryl, $C_{1-12}$ alkylamino, $C_{3-7}$ cycloalkylamino, Di($C_{1-12}$ alkyl) amino, $C_{3-7}$ cycloalkyl, and substituted $C_{3-7}$ cycloalkyl.

The numbers of $R_5$ and $R_6$ range from 0 to 6 while the optimal number is 0-3 or 0-2. If there are more than two $R_5$ and $R_6$, they are independent of each other.

$R_5$ and $R_6$ are separately selected from hydrogen, fluorine, chlorine, bromine, iodine, cyano, nitro, hydroxyl, hydroxyl, $C_{1-12}$ alkyl, $C_{1-12}$ alkoxy, $C_{3-7}$ cycloalkyl, halogenated $C_{1-12}$ alkyl, $C_{2-12}$ alkenyl, hydroxyl-substituted $C_{1-12}$ alkyl, $C_{1-12}$ alkylamino, $C_{3-7}$ cycloalkylamino, Di($C_{1-12}$ alkyl)amino, amino-$C_{1-12}$ alkylamino, $C_{1-12}$ alkoxy, $C_{1-12}$ alkylamino, $C_{1-12}$ alkoxycarbonyl, Di($C_{1-12}$ alkoxy-$C_{1-12}$ alkyl) amino, aminocarbonyl, $C_{1-12}$ alkylaminocarbonyl, Di($C_{1-12}$ alkyl) aminocarbonyl, $C_{3-7}$ cycloalkylaminocarbonyl, $C_{3-7}$ cycloalkoxy, halogenated $C_{1-12}$ alkoxy, amino $C_{1-12}$ alkyl, amino $C_{1-12}$ alkyl, $C_{1-12}$ alkyl sulfone, $C_{2-12}$ alkenyl sulfone, $C_{3-7}$ cycloalkyl sulfone, halogenated $C_{3-7}$ cycloalkyl, heterocyclic oxy, piperidinylamino, N-methylpiperidin-4-carbonyl, piperazine-$C_{1-6}$ alkyl, formamide, and N-methyl piperidine carboxamide.

Further, X could be carbonyl, thiocarbonyl, or sulfonyl. Carbonyl is preferred.

Further, Y could be carbonyl, thiocarbonyl, or sulfonyl. Carbonyl is preferred.

Further, X substituents are in the β position of the naphthalene ring and N substituents (connected to Y, shown in Formula 1) are in the non-substituted para-position of the naphthalene ring. For example, if X is substituted at the 2-position, then Y-connected N is substituted at the 6-position. If X is substituted at the 3-position, then Y-connected N substituted at the 7-position. Numbered from the carbon next to the two symmetric carbon (the two carbons in the middle are not numbered), the carbons of 1, 4, 5, and 8 are the same (called α carbon, or α-position), while the carbons of 2,3, 6, 7 are the same (called β carbon, or β-position).

Further, $R_1$ and $R_2$ together with the adjacent nitrogen atom can form a pyrrole ring, tetrahydropyrrole ring, pyridine ring, tetrahydropyridine ring, piperidine ring, piperazine ring, oxazine ring, tetrahydrooxazide ring, morpholine ring. The ring structure formed above can be substituted by $C_{1-6}$ alkyl, substituted $C_{1-6}$ hydrocarbyl substitution, halogenated $C_{1-3}$ hydrocarbon group substitution.

Further, $R_1$ and $R_2$ can be independently selected from hydrogen, $C_{1-6}$ alkyl, $C_{1-6}$ alkoxy, cyclopropane, cyclohexane, $C_{1-4}$ alkoxycarbonyl, $C_{1-4}$ alkylcarbonyl, aminocarbonyl, $C_{1-4}$ alkylaminocarbonyl, nitro, oxazolyl, oxazolyl, pyridyl, dihydropyridyl, tetrahydropyridyl, piperidinyl, thiazinyl, pyrrolyl, imidazolyl, pyrimidinyl, piperazinyl, pyrazolyl, morpholinyl, furanyl, pyranyl, phenyl, $C_{1-4}$ alkyl substituted phenyl, and $Di(C_{1-4}$ alkyl) substituted phenyl.

Further, $R_3$ can be selected from hydrogen, fluorine, chlorine, bromine, iodine, nitro, amino, methyl, ethyl, propyl, isopropyl, new butyl, cyclopropyl, cyclohexyl, halogenated cyclopropyl, halogenated cyclohexyl, halogenated $C_{1-6}$ alkyl, $C_{2-4}$ alkenyl, hydroxyl-substituted $C_{1-6}$ alkyl, $C_{1-6}$ alkoxy, $C_{1-6}$ alkoxycarbonyl, aminocarbonyl, $C_{1-4}$ alkylaminocarbonyl, $Di(C_{1-4}$ alkyl)aminocarbonyl, $C_{3-6}$ cycloalkylaminocarbonyl, $C_{3-6}$ cycloalkoxy, hydroxy-$C_{1-4}$ alkoxy, halogenated $C_{1-4}$ alkoxy, amino $C_{1-4}$ alkyl, amino $C_{1-4}$ alkoxy, $C_{1-4}$ alkyl sulfone, $C_{2-4}$ alkenyl sulfone, $C_{3-6}$ cycloalkyl sulfone, heterocyclic oxy, amino-substituted piperidinyl, N-methylpiperidin-4-carbonyl, piperazine-$C_{1-12}$ alkyl, formamide, and N-methyl piperidine carboxamide.

Further, $R_4$ can be selected from hydrogen, $C_{1-6}$ alkyl, halogenated $C_{1-6}$ alkyl, $C_{1-6}$ alkoxy, halogenated $C_{1-6}$ alkoxy, cyclopropyl, cyclopentyl, cyclohexyl, halogen substituted $C_{3-6}$ cycloalkyl, $C_{1-4}$ alkoxycarbonyl, $C_{1-6}$ alkylcarbonyl, aminocarbonyl, $C_{1-6}$ alkylcarbonyl, nitro, amino, $C_{1-3}$ alkyl substituted amino, $Di(C_{1-3}$ alkyl) substituted amino, oxazolyl, thiazinyl, pyridyl, dihydropyridyl, tetrahydropyridyl, piperidinyl, thiazinyl, pyrrolyl, imidazolyl, pyrazolyl, pyrazolyl, piperazinyl, morpholinyl, furanyl, pyranyl, phenyl, halogenated phenyl, benzyl, ethyl phenyl, dimethylphenyl, diethylphenyl, methyl (ethyl) phenyl, halogenated phenyl, and halomethylphenyl.

Further, $R_5$ and $R_6$ are hydrogen, halogen atoms, methyl, ethyl, and/or propyl. Preferably, $R_5$ and $R_6$ are hydrogen. When $R_5$ and $R_6$ are both hydrogen, there are no other substituents on naphthalene rings except diamides.

Further, $R_1$ and $R_2$ together with adjacent ring atoms can form a ring with 3-8 ring atoms and a substituted ring structure. A preferred structure is a 4-methyl-piperazinyl group or N-morpholinyl group.

Further, when neither $R_1$ or $R_2$ is hydrogen, $R_1$ and $R_2$ are both methyl groups.

Further, when one of $R_1$ and $R_2$ is hydrogen, the other one can be selected from one of the following groups: methyl, ethyl, propyl, butyl, $C_{1-4}$ alkyl substituted thiazolyl, thiazinyl, 2-thiazolyl or thiazol-2-yl, $C_{1-4}$ alkyl substituted phenyl, trifluoromethylphenyl, meta-trifluoromethylphenyl, $C_{1-4}$ alkyl substituted pyridyl, 6-chloro-piperidin-3-yl, 2-chloro-pyridin-5-yl, isopropyl, cyclopropyl, cyclohexyl, cyclohexane, and $C_{1-4}$ alkyl substituted cyclohexyl.

Further, $R_4$ can be selected from the following groups: 4-fluorophenyl, P-fluorophenyl, difluoro substituted phenyl, 3-methylphenyl, M-methylphenyl, P-methylphenyl, O-methylphenyl, ethyl phenyl, propyl phenyl, tert-butylphenyl, 2-methoxyphenyl, o-methoxyphenyl, ethoxyphenyl, di(ethoxy)phenyl, butyloxyphenyl, p-methoxyphenyl, methoxy phenyl, meta-trifluoromethylphenyl, P-trifluoromethylphenyl, 2,5-dimethoxyphenyl, M-chlorophenyl, P-chlorophenyl, 3,4-dichlorophenyl, trichloro-substituted phenyl, other halogen-substituted phenyl, $C_{1-4}$ alkyl substituted phenyl, $C_{1-4}$ alkoxy substituted phenyl, and $C_{2-6}$ alkenyl substituted phenyl.

Specifically, the naphthalene diamide compound of the present disclosure can be one of the compounds in the following table, wherein X and Y are both carbonyl groups, $R_5$ and $R_6$ are hydrogen, and $R_3$ is hydrogen.

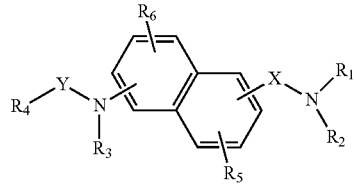

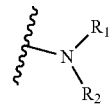

| Number | $R_4$ | $\begin{array}{c}\phantom{x}\\ \text{-N}{<}R_1/R_2\end{array}$ |
|---|---|---|
| ABC-01 | p-fluorophenyl | N-methyl-1-piperazinyl |
| ABC-02 | p-fluorophenyl | 2-thiazolimine |
| ABC-03 | p-fluorophenyl | meta-trifluoromethyl phenylenimine |
| ABC-04 | p-methoxyphenyl | N-methyl-1-piperazinyl |
| ABC-05 | m-methylphenyl | N-methyl-1-piperazinyl |
| ABC-06 | o-methoxyphenyl | N-methyl-1-piperazinyl |
| ABC-07 | p-fluorophenyl | 6-chloro-pyridine-3-methyleneamino |
| ABC-08 | methoxy phenyl | 6-chloro-pyridine-3-methyleneamino |
| ABC-09 | m-methylphenyl | 6-chloro-pyridine-3-methyleneamino |
| ABC-10 | o-methoxyphenyl | 6-chloro-pyridine-3-methyleneamino |
| ABC-11 | p-fluorophenyl | N-morpholinyl |
| ABC-12 | p-methoxyphenyl | N-morpholinyl |
| ABC-13 | m-methylphenyl | N-morpholinyl |
| ABC-14 | o-methoxyphenyl | N-morpholinyl |
| ABC-15 | 2,5-dimethoxyphenyl | 6-chloro-pyridine-3-methyleneamino |
| ABC-16 | 2,5-dimethoxyphenyl | N-morpholinyl |
| ABC-17 | meta-trifluoromethylphenyl | 6-chloro-pyridine-3-methyleneamino |
| ABC-18 | meta-trifluoromethylphenyl | N-morpholinyl |
| ABC-19 | 2,5-dimethoxyphenyl | N-methyl-1-piperazinyl |
| ABC-20 | meta-trifluoromethylphenyl | N-methyl-1-piperazinyl |
| ABC-21 | p-fluorophenyl | cyclopropylimine |
| ABC-22 | p-fluorophenyl | cyclohexylimine |
| ABC-23 | p-methoxyphenyl | cyclohexylimine |
| ABC-24 | meta-trifluoromethylphenyl | cyclohexylimine |
| ABC-26 | meta-trifluoromethylphenyl | meta-trifluoromethyl phenylenimine |
| ABC-27 | p-methoxyphenyl | cyclopropylimine |
| ABC-28 | meta-trifluoromethylphenyl | cyclopropylimine |
| ABC-29 | p-methoxyphenyl | isopropylimine |
| ABC-30 | meta-trifluoromethylphenyl | isopropylimine |
| ABC-31 | p-methoxyphenyl | 2-thiazolimine |
| ABC-32 | m-methylphenyl | 2-thiazolimine |
| ABC-33 | p-methoxyphenyl | meta-trifluoromethyl phenylenimine |
| ABC-34 | meta-trifluoromethylphenyl | 2-thiazolimine |
| ABC-36 | p-fluorophenyl | isopropylimine |
| ABC-37 | m-methylphenyl | isopropylimine |
| ABC-38 | o-methoxyphenyl | isopropylimine |
| ABC-39 | m-chlorophenyl | N-morpholinyl |
| ABC-40 | 3,4-dichlorophenyl | N-morpholinyl |
| ABC-41 | m-chlorophenyl | N-methyl-1-piperazinyl |
| ABC-42 | 3,4-dichlorophenyl | N-methyl-1-piperazinyl |
| ABC-43 | m-chlorophenyl | cyclopropylimine |
| ABC-44 | 3,4-dichlorophenyl | cyclopropylimine |
| ABC-45 | m-chlorophenyl | 2-thiazolimine |
| ABC-46 | 3,4-dichlorophenyl | 2-thiazolimine |
| ABC-47 | m-chlorophenyl | isopropylimine |
| ABC-48 | 3,4-dichlorophenyl | isopropylimine |
| ABC-50 | o-methoxyphenyl | 2-thiazolimine |

Further, the naphthalene diamide compound of the present disclosure may also be one of the compounds in the following table, wherein X and Y are both sulfonyl groups or one of them is a sulfonyl group and the other is a carbonyl group, while $R_5$ and $R_6$ are hydrogen or a simple alkyl group, and $R_3$ is hydrogen.

| ID | X | Y | R4 | R1/R2 | R5 | R6 |
|---|---|---|---|---|---|---|
| ABC-51 | sulfonyl | carbonyl | p-fluorophenyl | N-methyl-1-piperazinyl | methyl | ethyl |
| ABC-52 | carbonyl | sulfonyl | | | isopropyl | methyl |
| ABC-53 | sulfonyl | sulfonyl | | | ethyl | isopropyl |
| ABC-54 | sulfonyl | carbonyl | P-fluorophenyl | 2-thiazolimine | methyl | ethyl |
| ABC-55 | carbonyl | sulfonyl | P-fluorophenyl | | isopropyl | methyl |
| ABC-56 | sulfonyl | sulfonyl | P-fluorophenyl | | ethyl | isopropyl |
| ABC-57 | sulfonyl | carbonyl | p-fluorophenyl | meta-trifluoromethyl phenylenimine | methyl | ethyl |
| ABC-58 | carbonyl | sulfonyl | | | isopropyl | methyl |
| ABC-59 | sulfonyl | sulfonyl | | | ethyl | isopropyl |
| ABC-60 | sulfonyl | carbonyl | p-methoxyphenyl | N-methyl-1-piperazinyl | methyl | ethyl |
| ABC-61 | carbonyl | sulfonyl | | N-methyl-1-piperazinyl | isopropyl | methyl |
| ABC-62 | sulfonyl | sulfonyl | | N-methyl-1-piperazinyl | ethyl | isopropyl |
| ABC-63 | sulfonyl | carbonyl | m-methylphenyl | N-methyl-1-piperazinyl | methyl | ethyl |
| ABC-64 | carbonyl | sulfonyl | | | isopropyl | methyl |
| ABC-65 | sulfonyl | sulfonyl | | | ethyl | isopropyl |
| ABC-66 | sulfonyl | carbonyl | o-methoxyphenyl | N-methyl-1-piperazinyl | methyl | Ethyl |
| ABC-67 | carbonyl | sulfonyl | | | isopropyl | methyl |
| ABC-68 | sulfonyl | sulfonyl | | | ethyl | isopropyl |
| ABC-69 | sulfonyl | carbonyl | p-fluorophenyl | 6-chloro-pyridine-3-methyleneamino | methyl | Ethyl |
| ABC-70 | carbonyl | sulfonyl | | | isopropyl | methyl |
| ABC-71 | sulfonyl | sulfonyl | | | ethyl | isopropyl |
| ABC-72 | sulfonyl | carbonyl | methoxy phenyl | 6-chloro-pyridine-3-methyleneamino | methyl | ethyl |
| ABC-73 | carbonyl | sulfonyl | | | isopropyl | methyl |
| ABC-74 | sulfonyl | sulfonyl | | | ethyl | isopropyl |
| ABC-76 | sulfonyl | carbonyl | m-methylphenyl | 6-chloro-pyridine-3-methyleneamino | methyl | ethyl |
| ABC-77 | carbonyl | sulfonyl | | | isopropyl | methyl |
| ABC-78 | sulfonyl | sulfonyl | | | ethyl | isopropyl |
| ABC-79 | sulfonyl | carbonyl | o-methoxyphenyl | 6-chloro-pyridine-3-methyleneamino | methyl | ethyl |
| ABC-80 | carbonyl | sulfonyl | | | isopropyl | methyl |
| ABC-81 | sulfonyl | sulfonyl | | | ethyl | isopropyl |
| ABC-82 | sulfonyl | carbonyl | p-fluorophenyl | N-morpholinyl | methyl | ethyl |
| ABC-83 | carbonyl | sulfonyl | | N-morpholinyl | isopropyl | methyl |
| ABC-84 | sulfonyl | sulfonyl | | N-morpholinyl | ethyl | isopropyl |
| ABC-85 | sulfonyl | carbonyl | p-methoxyphenyl | N-morpholinyl | methyl | ethyl |
| ABC-86 | carbonyl | sulfonyl | | N-morpholinyl | isopropyl | methyl |
| ABC-87 | sulfonyl | sulfonyl | | N-morpholinyl | ethyl | isopropyl |
| ABC-88 | sulfonyl | carbonyl | m-methylphenyl | N-morpholinyl | methyl | ethyl |
| ABC-89 | carbonyl | sulfonyl | | N-morpholinyl | isopropyl | methyl |
| ABC-90 | sulfonyl | sulfonyl | | N-morpholinyl | ethyl | isopropyl |
| ABC-91 | sulfonyl | carbonyl | o-methoxyphenyl | N-morpholinyl | methyl | ethyl |
| ABC-92 | carbonyl | sulfonyl | | | isopropyl | methyl |
| ABC-93 | sulfonyl | sulfonyl | | | ethyl | isopropyl |
| ABC-94 | sulfonyl | carbonyl | 2,5-dimethoxyphenyl | 6-chloro-pyridine-3-methyleneamino | methyl | ethyl |
| ABC-95 | carbonyl | sulfonyl | | | isopropyl | methyl |
| ABC-96 | sulfonyl | sulfonyl | | | ethyl | isopropyl |
| ABC-97 | sulfonyl | carbonyl | 2,5-dimethoxyphenyl | N-morpholinyl | methyl | ethyl |
| ABC-98 | carbonyl | sulfonyl | | | isopropyl | methyl |
| ABC-99 | sulfonyl | sulfonyl | | | ethyl | isopropyl |
| ABC-100 | sulfonyl | carbonyl | meta-trifluoromethylphenyl | 6-chloro-pyridine-3-methyleneamino | methyl | ethyl |
| ABC-101 | carbonyl | sulfonyl | | | isopropyl | methyl |
| ABC-102 | sulfonyl | sulfonyl | | | Ethyl | isopropyl |
| ABC-103 | sulfonyl | carbonyl | meta-trifluoromethylphenyl | N-morpholinyl | methyl | ethyl |
| ABC-104 | carbonyl | sulfonyl | | | isopropyl | methyl |
| ABC-105 | sulfonyl | sulfonyl | | | ethyl | isopropyl |
| ABC-106 | sulfonyl | carbonyl | 2,5-dimethoxyphenyl | N-methyl-1-piperazinyl | methyl | ethyl |
| ABC-107 | carbonyl | sulfonyl | | N-methyl-1-piperazinyl | isopropyl | methyl |
| ABC-108 | sulfonyl | sulfonyl | | N-methyl-1-piperazinyl | Ethyl | isopropyl |
| ABC-109 | sulfonyl | carbonyl | meta-trifluoromethylphenyl | N-methyl-1-piperazinyl | methyl | ethyl |
| ABC-110 | carbonyl | sulfonyl | | | isopropyl | methyl |
| ABC-111 | sulfonyl | sulfonyl | | | ethyl | isopropyl |
| ABC-112 | sulfonyl | carbonyl | p-fluorophenyl | cyclopropylimine | methyl | ethyl |
| ABC-113 | carbonyl | sulfonyl | | | isopropyl | methyl |
| ABC-114 | sulfonyl | sulfonyl | | | ethyl | isopropyl |
| ABC-115 | sulfonyl | carbonyl | p-fluorophenyl | cyclohexylimine | methyl | ethyl |
| ABC-116 | carbonyl | sulfonyl | | cyclohexylimine | isopropyl | methyl |

-continued

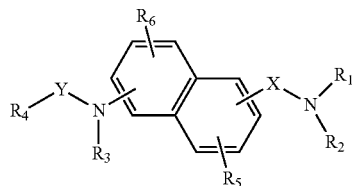

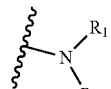

| ID | X | Y | R4 | R1/R2 | R5 | R6 |
|---|---|---|---|---|---|---|
| ABC-117 | sulfonyl | sulfonyl | | cyclohexylimine | ethyl | isopropyl |
| ABC-118 | sulfonyl | carbonyl | p-methoxyphenyl | cyclohexylimine | methyl | ethyl |
| ABC-119 | carbonyl | sulfonyl | | cyclohexylimine | isopropyl | methyl |
| ABC-120 | sulfonyl | sulfonyl | | cyclohexylimine | ethyl | isopropyl |
| ABC-121 | sulfonyl | carbonyl | meta-trifluoromethylphenyl | cyclohexylimine | methyl | ethyl |
| ABC-122 | carbonyl | sulfonyl | meta-trifluoromethylphenyl | | isopropyl | methyl |
| ABC-123 | sulfonyl | sulfonyl | meta-trifluoromethylphenyl | | ethyl | isopropyl |
| ABC-124 | sulfonyl | carbonyl | meta-trifluoromethylphenyl | m-trifluoromethyl benzylimino | methyl | ethyl |
| ABC-125 | carbonyl | sulfonyl | | | isopropyl | methyl |
| ABC-126 | sulfonyl | sulfonyl | | | ethyl | isopropyl |
| ABC-127 | sulfonyl | carbonyl | P-methoxyphenyl | cyclopropylimine | methyl | ethyl |
| ABC-128 | carbonyl | sulfonyl | | cyclopropylimine | isopropyl | methyl |
| ABC-129 | sulfonyl | sulfonyl | | cyclopropylimine | ethyl | isopropyl |
| ABC-130 | sulfonyl | carbonyl | Meta-trifluoromethylphenyl | cyclopropylimine | methyl | ethyl |
| ABC-131 | carbonyl | sulfonyl | | | isopropyl | methyl |
| ABC-132 | sulfonyl | sulfonyl | | | ethyl | isopropyl |
| ABC-133 | sulfonyl | carbonyl | p-methoxyphenyl | isopropylimine | methyl | ethyl |
| ABC-134 | carbonyl | sulfonyl | | isopropylimine | isopropyl | methyl |
| ABC-135 | sulfonyl | sulfonyl | | isopropylimine | ethyl | isopropyl |
| ABC-136 | sulfonyl | carbonyl | meta-trifluoromethylphenyl | isopropylimine | methyl | ethyl |
| ABC-137 | carbonyl | sulfonyl | | | isopropyl | methyl |
| ABC-138 | sulfonyl | sulfonyl | | | ethyl | isopropyl |
| ABC-139 | sulfonyl | carbonyl | p-methoxyphenyl | 2-thiazolimine | methyl | ethyl |
| ABC-140 | carbonyl | sulfonyl | | 2-thiazolimine | isopropyl | methyl |
| ABC-141 | sulfonyl | sulfonyl | | 2-thiazolimine | ethyl | isopropyl |
| ABC-142 | sulfonyl | carbonyl | m-methylphenyl | 2-thiazolimine | methyl | ethyl |
| ABC-143 | carbonyl | sulfonyl | | | isopropyl | methyl |
| ABC-144 | sulfonyl | sulfonyl | | | ethyl | isopropyl |
| ABC-145 | sulfonyl | carbonyl | p-methoxyphenyl | meta-trifluoromethyl phenylenimine | methyl | ethyl |
| ABC-146 | carbonyl | sulfonyl | | | isopropyl | methyl |
| ABC-147 | sulfonyl | sulfonyl | | | Ethyl | isopropyl |
| ABC-148 | sulfonyl | carbonyl | meta-trifluoromethylphenyl | 2-thiazolimine | methyl | Ethyl |
| ABC-149 | carbonyl | sulfonyl | | | isopropyl | methyl |
| ABC-150 | sulfonyl | sulfonyl | | | ethyl | isopropyl |
| ABC-151 | sulfonyl | carbonyl | p-fluorophenyl | isopropylimine | methyl | ethyl |
| ABC-152 | carbonyl | sulfonyl | | | isopropyl | methyl |
| ABC-153 | sulfonyl | sulfonyl | | | ethyl | isopropyl |
| ABC-154 | sulfonyl | carbonyl | m-methylphenyl | isopropylimine | methyl | ethyl |
| ABC-155 | carbonyl | sulfonyl | | isopropylimine | isopropyl | methyl |
| ABC-156 | sulfonyl | sulfonyl | | isopropylimine | ethyl | isopropyl |
| ABC-157 | sulfonyl | carbonyl | o-methoxyphenyl | isopropylimine | methyl | ethyl |
| ABC-158 | carbonyl | sulfonyl | | | isopropyl | methyl |
| ABC-159 | sulfonyl | sulfonyl | | | ethyl | isopropyl |
| ABC-160 | sulfonyl | carbonyl | m-chlorophenyl | N-morpholinyl | methyl | ethyl |
| ABC-161 | carbonyl | sulfonyl | | N-morpholinyl | isopropyl | methyl |
| ABC-162 | sulfonyl | sulfonyl | | N-morpholinyl | ethyl | isopropyl |
| ABC-163 | sulfonyl | carbonyl | 3,4-dichlorophenyl | N-morpholinyl | methyl | ethyl |
| ABC-164 | carbonyl | sulfonyl | | | isopropyl | methyl |
| ABC-165 | sulfonyl | sulfonyl | | | ethyl | isopropyl |
| ABC-166 | sulfonyl | carbonyl | m-chlorophenyl | N-methyl-1-piperazinyl | methyl | ethyl |
| ABC-167 | carbonyl | sulfonyl | | N-methyl-1-piperazinyl | isopropyl | methyl |
| ABC-168 | sulfonyl | sulfonyl | | N-methyl-1-piperazinyl | ethyl | isopropyl |
| ABC-169 | sulfonyl | carbonyl | 3,4-dichlorophenyl | N-methyl-1-piperazinyl | methyl | ethyl |
| ABC-170 | carbonyl | sulfonyl | | | isopropyl | methyl |
| ABC-171 | sulfonyl | sulfonyl | | | ethyl | isopropyl |
| ABC-172 | sulfonyl | carbonyl | m-chlorophenyl | cyclopropylimine | methyl | ethyl |
| ABC-173 | carbonyl | sulfonyl | | cyclopropylimine | isopropyl | methyl |
| ABC-174 | sulfonyl | sulfonyl | | cyclopropylimine | ethyl | isopropyl |
| ABC-175 | sulfonyl | carbonyl | 3,4-dichlorophenyl | cyclopropylimine | methyl | ethyl |
| ABC-176 | carbonyl | sulfonyl | | | isopropyl | methyl |
| ABC-177 | sulfonyl | sulfonyl | | | ethyl | isopropyl |

-continued

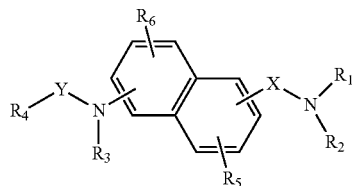

| ID | X | Y | R$_4$ | 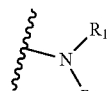 | R$_5$ | R$_6$ |
|---|---|---|---|---|---|---|
| ABC-178 | sulfonyl | carbonyl | m-chlorophenyl | 2-thiazolimine | methyl | ethyl |
| ABC-179 | carbonyl | sulfonyl | | 2-thiazolimine | isopropyl | methyl |
| ABC-180 | sulfonyl | sulfonyl | | 2-thiazolimine | ethyl | isopropyl |
| ABC-181 | sulfonyl | carbonyl | 3,4-dichlorophenyl | 2-thiazolimine | methyl | ethyl |
| ABC-182 | carbonyl | sulfonyl | | | isopropyl | methyl |
| ABC-183 | sulfonyl | sulfonyl | | | ethyl | isopropyl |
| ABC-184 | sulfonyl | Carbonyl | m-chlorophenyl | isopropylimine | methyl | ethyl |
| ABC-185 | carbonyl | sulfonyl | | | isopropyl | methyl |
| ABC-186 | sulfonyl | sulfonyl | | | ethyl | isopropyl |
| ABC-187 | sulfonyl | carbonyl | 3,4-dichlorophenyl | isopropylimine | methyl | ethyl |
| ABC-188 | carbonyl | sulfonyl | | | isopropyl | methyl |
| ABC-189 | sulfonyl | Sulfonyl | | | ethyl | isopropyl |
| ABC-190 | sulfonyl | carbonyl | o-methoxyphenyl | 2-thiazolimine | methyl | ethyl |
| ABC-191 | carbonyl | sulfonyl | | | isopropyl | methyl |
| ABC-192 | sulfonyl | sulfonyl | | | ethyl | isopropyl |

The present disclosure also provides a process for preparation of the compounds of Formula I mentioned above.

A method for synthesizing the above naphthalene diamide compound, comprising:

Substituting aromatic acid or other organic carboxylic acid in a solvent of dichloromethane and participating in the reaction, catalyzing with a small amount of DMF, stirring the reaction for several hours to form a series of acid chloride (the first compound (1) in the following reaction scheme);

The acid chloride is then immediately introduced into the carboxy-substituted naphthylamine. The reaction is carried out under the catalysis of THF (tetrahydrofuran) and DIEA (N, N-Di-Isopropylethylamine) to obtain a series of carboxy-substituted naphthlamide (the following reaction) as the second compound (2) in this process;

The second compound and substituted amine was under stirring reaction catalyzed by EDCI (1-Ethyl-(3-dimethylaminopropyl) carbodiimide) and DMAP (4-dimethylaminopyridine) using THF as the solvent. A series of naphthalene diamide (the third product (3) shown in the following reaction scheme) was obtained.

The reaction process is shown as follows:

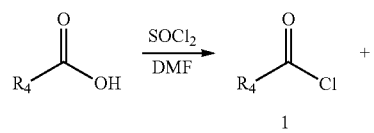

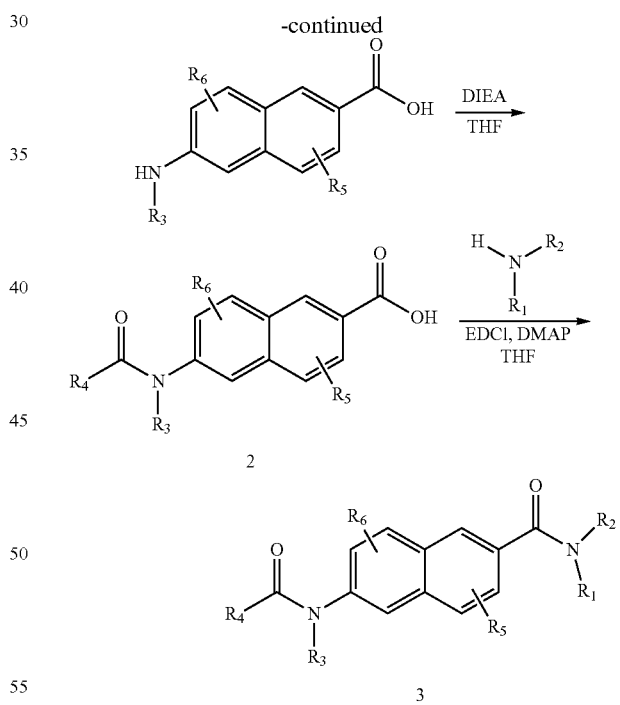

A drug comprises the above compound of Formula I or a pharmaceutically acceptable salt or ester with the compound as active ingredients. Any number and combination of the above compounds, salt, or ester form can be selected as active ingredients to produce the drug for treating tumor diseases with antibacterial, antiviral, and anti-inflammatory properties.

Compared with the prior scheme, the beneficial effects of the present disclosure are shown as follows: the present disclosure provides a novel compound based on the structure of Formula I, which can be effectively applied to treat and prevent tumor diseases caused by abnormal growth of various human cells.

The present disclosure will be further described in detail by the following case as proof-of-concept examples. However, the scope of the present disclosure is not to be limited to the following embodiments.

Example 1, preparation of compound as Formula 1

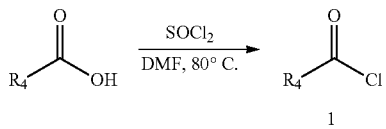

1.496 g (11 mmol) of m-methylbenzoic acid was placed in a 50 mL round bottom flask, about 11 mL of dichlorosulfoxide was added, and 3-4 drops of DMF were added to catalyze the reaction. The mixture was refluxed at 80° C. for 3 h. Thin layer chromatography (TLC) was used to follow the progress of the reaction. After the reaction was completed, the mixture was cooled to room temperature, and the excess $SOCl_2$ solvent was removed by rotary evaporation to obtain m-methylbenzoyl chloride.

Example 2, preparation of compound as formula 2

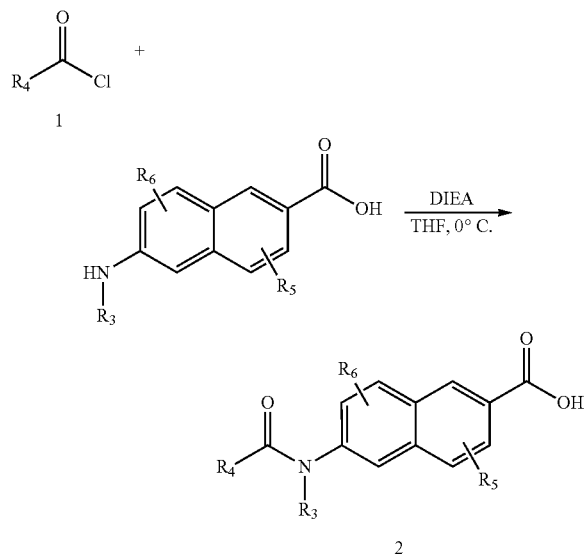

1.496 g (8 mmol) of 6-aminonaphthoic acid was added to the flask, dissolved in THF. 16 mmol of DIEA was added, and the solution was stirred and kept at 0° C. to obtain the m-methylbenzoyl chloride, which was subsequently dissolved in DCM and slowly added dropwise to the above mixed solution. Thin layer chromatography (TLC) was used to monitor the whole progress of the reaction. After the reaction was completed, the organic phase was concentrated by spin-drying to obtain a solid powder, and a small amount of diluted hydrochloric acid acidified solution was added, maintaining the pH of solution as weak acidic. The solid was filtered and washed 2-3 times with water. The crude compound 2a was obtained.

Example 3, preparation of compound as formula 3

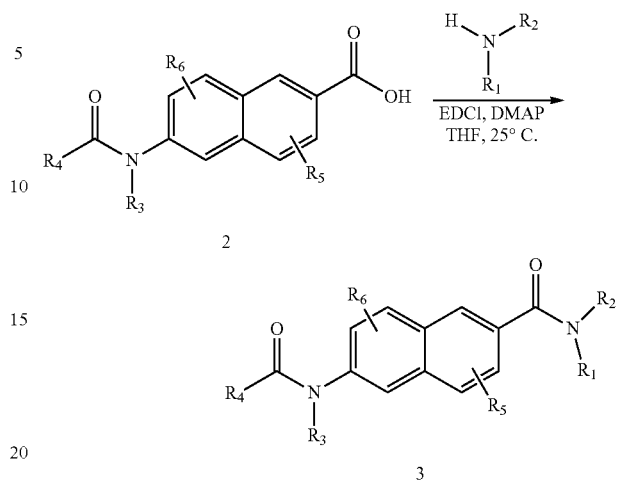

76.5 mg (0.25 mmol) of Compound 2a, 95 mg (0.5 mmol) of EDCI, and 30 mg (0.25 mmol) of DMAP were dissolved in tetrahydrofuran and stirred at room temperature for 15 min. Then 35.5 mg (0.25 mmol) of 5-aminomethyl-2-chloropyridine was added. The reaction was stirred at room temperature for about 6 h with the column separation for obtaining the final product ABC-09.

Example 4, using the synthesis method above by the schemes in examples 1-3, the compounds labelled ABC-1 to ABC-192 were separately synthesized and characterized. The NMR (nuclear magnetic resonance) and MS (mass spectrometry) data of the compounds were shown as follows:

ABC-01: $^1$H-NMR (DMSO-$d_6$, 400 MHz): δ 11.05-10.18 (m, 1H), 8.82-7.13 (m, 10H), 2.50 (p, J=1.8 Hz, 6H), 2.38 (s, 4H), 2.23 (s, 2H) ppm. HRMS (ESI) m/z: (M+H)$^+$ calcd for $C_{23}H_{22}FN_3O_2$: 390.5; found: 390.2.

ABC-02: $^1$H-NMR (DMSO-$d_6$, 400 MHz): δ 12.73 (s, 1H), 10.62 (s, 1H), 8.74 (d, J=1.8 Hz, 1H), 8.56 (d, J=2.0 Hz, 1H), 8.19-7.90 (m, 6H), 7.59 (d, J=3.6 Hz, 1H), 7.46-7.25 (m, 3H) ppm. HRMS (ESI) m/z: (M+H)$^+$ calcd for $C_{21}H_{14}FN_3O_2S$: 390.4; found: 390.3.

ABC-03: $^1$H-NMR (DMSO-$d_6$, 400 MHz): δ 10.70 (s, 1H), 10.60 (s, 1H), 8.57 (s, 2H), 8.30 (s, 1H), 8.21-7.84 (m, 7H), 7.63 (t, J=8.0 Hz, 1H), 7.54-7.33 (m, 3H) ppm. HRMS (ESI) m/z: (M+H)$^+$ calcd for $C_{25}H_{16}F_4N_2O_2$: 451.4; found: 451.2.

ABC-04: $^1$H-NMR (DMSO-$d_6$, 400 MHz): δ 8.30 (d, J=2.1 Hz, 1H), 8.00 (s, 1H), 7.90-7.68 (m, 5H), 7.46-7.34 (m, 1H), 7.19 (s, 1H), 6.93 (d, J=8.5 Hz, 2H), 3.82 (s, 3H), 3.81-2.99 (m, 4H), 2.66-2.12 (m, 4H), 1.19 (s, 3H) ppm. HRMS (ESI) m/z: (M+H)$^+$ calcd for $C_{24}H_{25}N_3O_3$: 402.5; found: 402.3.

ABC-05: $^1$H-NMR (DMSO-$d_6$, 400 MHz): δ 10.48 (s, 1H), 8.52 (d, J=2.0 Hz, 1H), 8.12-7.83 (m, 6H), 7.56-7.39 (m, 3H), 3.33 (s, 3H), 2.50 (p, J=1.8 Hz, 2H), 2.39 (s, 5H), 2.11 (d, J=99.2 Hz, 4H) ppm. HRMS (ESI) m/z: (M+H)$^+$ calcd for $C_{24}H_{25}N_3O_2$ 386.5; found: 386.3.

ABC-06: $^1$H-NMR (DMSO-$d_6$, 400 MHz): δ 10.39 (s, 1H), 8.53 (d, J=2.0 Hz, 1H), 3.93 (s, 3H), 3.78 (s, 4H), 2.55-2.49 (m, 5H), 2.19 (d, J=12.8 Hz, 5H) ppm. HRMS (ESI) m/z: (M+H)$^+$ calcd for $C_{24}H_{25}N_3O_3$: 402.5; found: 402.2.

ABC-07: $^1$H-NMR (DMSO-$d_6$, 400 MHz): δ 10.56 (s, 1H), 9.23 (t, J=5.9 Hz, 1H), 8.58-8.50 (m, 1H), 8.43 (d, J=3.4 Hz, 2H), 8.15-7.84 (m, 7H), 7.58-7.31 (m, 3H), 4.54

(d, J=5.8 Hz, 2H) ppm. HRMS (ESI) m/z: (M+H)$^+$ calcd for C$_{24}$H$_{17}$ClFN$_3$O$_2$: 432.9; found: 432.2.

ABC-08: $^1$H-NMR (DMSO-d$_6$, 400 MHz): δ 10.39 (s, 1H), 9.23 (t, J=6.0 Hz, 1H), 8.47 (d, J=34.1 Hz, 3H), 8.12-7.75 (m, 7H), 7.50 (d, J=8.2 Hz, 1H), 7.10 (d, J=8.5 Hz, 2H), 4.54 (d, J=5.8 Hz, 2H), 3.86 (s, 3H) ppm. HRMS (ESI) m/z: (M+H)$^+$ calcd for C$_{25}$H$_{20}$ClN$_3$O$_3$: 444.9; found: 444.3.

ABC-09: $^1$H-NMR (DMSO-d$_6$, 400 MHz): δ 10.51 (s, 1H), 9.23 (t, J=5.9 Hz, 1H), 8.53 (d, J=1.9 Hz, 1H), 8.43 (d, J=2.8 Hz, 2H), 8.08-7.75 (m, 8H), 7.60-7.42 (m, 2H), 4.55 (d, J=5.8 Hz, 2H), 2.43 (s, 3H) ppm. HRMS (ESI) m/z: calcd for C$_{25}$H$_{20}$ClN$_3$O$_2$: 428.9; found: 428.3.

ABC-10: $^1$H-NMR (DMSO-d$_6$, 400 MHz): δ 10.43 (s, 1H), 8.54 (d, J=2.0 Hz, 1H), 8.43 (d, J=2.0 Hz, 2H), 7.93 (d, J=1.2 Hz, 2H), 7.88-7.77 (m, 2H), 7.68 (dd, J=7.6, 1.8 Hz, 1H), 7.56-7.42 (m, 3H), 7.31-6.95 (m, 3H), 4.55 (d, J=5.8 Hz, 2H), 3.93 (s, 3H) ppm. HRMS (ESI) m/z: (M+H)$^+$ calcd for C$_{25}$H$_{20}$ClN$_3$O$_3$: 444.9; found: 444.2.

ABC-11: $^1$H-NMR (DMSO-d$_6$, 400 MHz): δ 10.37 (s, 1H), 8.51 (d, J=2.0 Hz, 1H), 8.17-7.70 (m, 6H), 7.49 (dd, J=8.4, 1.7 Hz, 1H), 7.39-6.89 (m, 2H), 3.86 (s, 3H), 3.48 (d, J=119.1 Hz, 8H) ppm. HRMS (ESI) m/z: (M+H)$^+$ calcd for C$_{23}$H$_{22}$N$_2$O$_4$: 389.4; found: 389.2.

ABC-12: $^1$H-NMR (DMSO-d$_6$, 400 MHz): δ 10.37 (s, 1H), 8.51 (d, J=2.0 Hz, 1H), 8.17-7.70 (m, 6H), 7.49 (dd, J=8.4, 1.7 Hz, 1H), 7.39-6.89 (m, 2H), 3.86 (s, 3H), 3.48 (d, J=119.1 Hz, 8H) ppm. HRMS (ESI) m/z: (M+H)$^+$ calcd for C$_{23}$H$_{22}$N$_2$O$_4$: 389.4; found: 389.2.

ABC-13: $^1$H-NMR (DMSO-d$_6$, 400 MHz): δ 8.32 (d, J=2.1 Hz, 1H), 8.07 (s, 1H), 7.84-7.56 (m, 5H), 7.43-7.28 (m, 3H), 7.19 (s, 1H), 3.66 (s, 8H), 2.39 (s, 3H) ppm. HRMS (ESI) m/z: calcd for C$_{23}$H$_{22}$N$_2$O$_3$: 373.4; found: 373.3.

ABC-14: $^1$H-NMR (DMSO-d$_6$, 400 MHz): δ 10.09 (s, 1H), 8.36 (dd, J=7.8, 1.8 Hz, 1H), 7.97-7.83 (m, 3H), 7.66-7.45 (m, 3H), 7.31-7.03 (m, 3H), 4.14 (s, 3H), 3.76 (s, 8H) ppm.HRMS (ESI) m/z: (M+H)$^+$ calcd for C$_{23}$H$_{22}$N$_2$O$_4$: 389.4; found: 389.3.

ABC-15: $^1$H-NMR (DMSO-d$_6$, 400 MHz): δ 10.24 (s, 1H), 8.47 (d, J=40.5 Hz, 2H), 8.28 (s, 1H), 7.85 (dd, J=20.3, 7.7 Hz, 4H), 7.59 (d, J=8.9 Hz, 1H), 7.41-7.24 (m, 2H), 7.18-6.98 (m, 2H), 6.80 (s, 1H), 4.82-4.59 (m, 2H), 4.09 (d, J=2.4 Hz, 3H), 3.88 (t, J=1.8 Hz, 3H) ppm. HRMS (ESI) m/z: calcd for C$_{26}$H$_{22}$ClN$_3$O$_4$: 474.9; found: 474.4.

Figure 2:
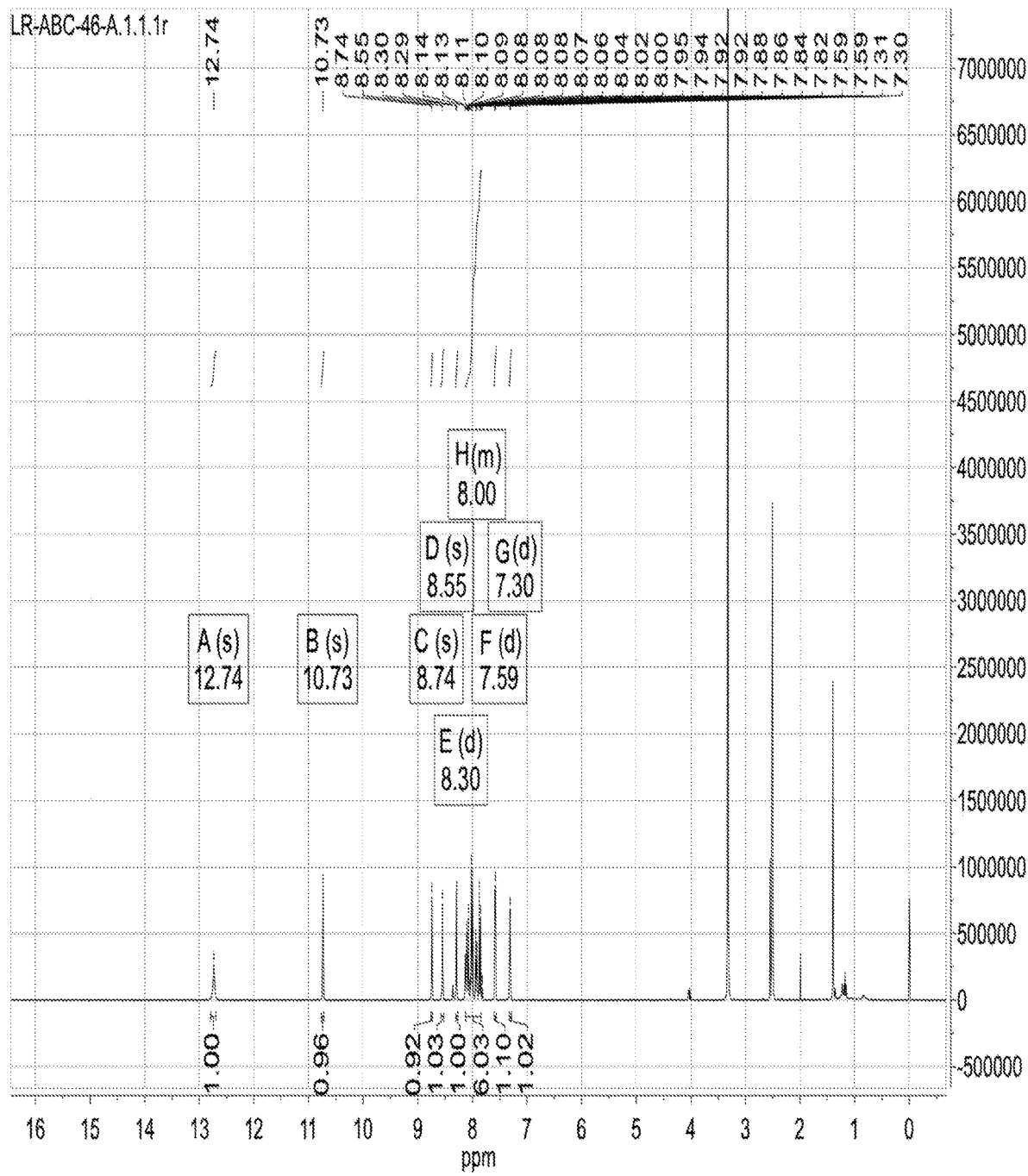
FIG. 2 illustrates an ABC-46 nuclear magnetic resonance spectrum of the compound and/or drug of the present disclosure.

A partial nuclear magnetic resonance spectrum is shown in FIG. 1 and FIG. 2, wherein FIG. 1 is the nuclear magnetic resonance spectrum of compound ABC-09 and FIG. 2 is the nuclear magnetic resonance spectrum of compound ABC-46. The compounds numbered ABC-51 to ABC-192 were synthesized according to the procedures of Examples 1-3 with quantitative analysis.

Case Study I: Antitumor Cell Activity of Naphthalene Diamides

Compounds of Tables 1 and 2 were synthesized in multiple steps according to the procedure of Examples 1-3 using relevant antitumor cell activity assays. The compound synthesized above was tested for IC$_{50}$ concentration (MIC) against HCT-116, MCF-7, Calu-6 and A549 tumor cells by in vitro cellular activity. The results are shown as follows.

Case Study II: Cell Proliferation Inhibition Assay

Based on MTT method, briefly plating HCT-116, MCF-7 and A549 cells in a concentration of 2×10$^4$/ml with complete culture medium in 96-well plates overnight. The volume for each well was 100 μL. Cells were treated with compounds in concentrations of 40, 20, 10, 5, 2.5, 1.25 μmol/L, and cultured at 37° C., 5% CO$_2$ for 48 hours, followed by adding 20 μL of 5 mg/ml MTT reagent per well and continuing to culture for 2~4 h, respectively. As a control, DMSO solvent was added in an equal volume with concentration of 0.1%. Each sample was tested as 5 replicate wells. Then the supernatant was discarded, and DMSO was added in a volume of 150 μL, followed by shaking and mixing for 15 mins. The absorbance (A) value (A value is proportional to the number of living cells) is measured by a microplate reader at the wavelength of 570 nm, and the average value is taken. The relative cell proliferation inhibition rate (%)=(control group A$_{570}$—experimental group A$_{570}$)/control group A$_{570}$×100%. The concentration of 50% inhibition rate (IC$_{50}$) of the compound was calculated by the repetition of at least 3 times. The positive control was used as 5-flucrouracil.

The results (μmol/L) are shown as follows:

| ID | HCT-116(IC$_{50}$) | MCF-7(IC$_{50}$) | Calu-6(IC$_{50}$) | A549(IC$_{50}$) |
|---|---|---|---|---|
| ABC-01 | | | | |
| ABC-02 | 10.0 | | | |
| ABC-03 | | | | |
| ABC-04 | | | | |
| ABC-05 | 10.0 | | | |
| ABC-06 | | | | |
| ABC-07 | 5.8 | 7.6 | | |
| ABC-08 | 10.0 | 10.9 | | |
| ABC-09 | 3.5 | 3.2 | | |
| ABC-10 | | | | |
| ABC-11 | 5.5 | 3.7 | | 28.104 |
| ABC-12 | | | | |
| ABC-13 | | | | |
| ABC-14 | | | | |
| ABC-15 | 6.6 | 3.5 | | |
| ABC-16 | | | | |
| ABC-17 | 3.6 | 3.2 | | |
| ABC-18 | | | | |
| ABC-19 | | | | |
| ABC-20 | 24.9 | 2.7 | | |
| ABC-21 | | | 48.5 | 48.502 |
| ABC-22 | | | | |
| ABC-23 | | | | |
| ABC-24 | 5 | | | |
| ABC-26 | 3.5 | | | |
| ABC-27 | 38.8 | 2.65 | | |
| ABC-28 | 5.0 | | | |
| ABC-29 | 8.0 | | | |
| ABC-30 | | | | |
| ABC-31 | | 3.9 | | |
| ABC-32 | 5.5 | 2.9 | 28.1 | 14.2 |
| ABC-33 | 3.0 | 6.6 | | |
| ABC-34 | 5.2 | 1.6 | | |
| ABC-36 | | | | |
| ABC-37 | | | | |
| ABC-38 | 5.0 | 9 | | |
| ABC-39 | | | | |
| ABC-40 | | | 12.4 | |
| ABC-41 | | | | |
| ABC-42 | 20.0 | | 7.1 | 3.7 |
| ABC-43 | | | 25.3 | 25.25 |
| ABC-44 | | | 5.5 | |
| ABC-45 | 10.0 | 6.7 | 12.6 | 4.3 |
| ABC-46 | 2.0 | 6.2 | | 1.6 |
| ABC-47 | 2.5 | | | 12.440 |
| ABC-48 | 3.9 | | | 12.629 |
| ABC-50 | | | | |

What is claimed:

1. A napththalene diamide compound of Formula I:

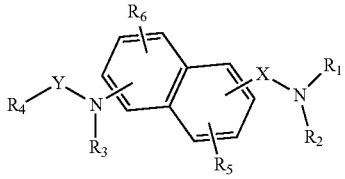

Formula I wherein:

X and Y are independently C(=O);

$R_1$ is —$CH_2$-pyridine, $C_3$-$C_7$ cycloalkyl, phenyl or thiazole, said $R_1$ being optionally substituted by 1-3 substituents independently selected from halogen and $C_{1-12}$ haloalkyl, and $R_2$ is H, or $R_1$ and $R_2$ together with the N atom to which they are attached form a piperazine or morpholine ring, said ring being optionally substituted by 1-3 substituents independently selected from halogen and $C_{1-12}$ alkyl;

$R_3$ is H;

$R_4$ is phenyl optionally substituted by 1-3 substituents independently selected from halogen, $C_{1-12}$ haloalkyl, and $C_{1-12}$ alkoxy; and $R_5$ and $R_6$ are independently H.

2. The naphthalene diamide compound of claim 1, wherein $R_4$ and —N($R_1$)($R_2$) are as in the following table:

| Number | $R_4$ | 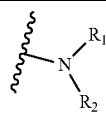 $R_1$ / $R_2$ |
|---|---|---|
| ABC-01 | p-fluorophenyl | N-methyl-1-piperazine |
| ABC-02 | p-fluorophenyl | 2-thiazole imino group |
| ABC-03 | p-fluorophenyl | Meta-trifluoromethyl phenylenimine |
| ABC-04 | P-methoxyphenyl | N-methyl-1-piperazinyl |
| ABC-05 | m-methyl phenyl | N-methyl-1-piperazinyl |
| ABC-06 | o-methoxyphenyl | N-methyl-1-piperazinyl |
| ABC-07 | p-fluorophenyl | 6-chloro-pyridine-3-methyleneamino |
| ABC-08 | methoxy phenyl | 6-chloro-pyridine-3-methyleneamino |
| ABC-09 | m-methylphenyl | 6-chloro-pyridine-3-methyleneamino |
| ABC-10 | o-methoxyphenyl | 6-chloro-pyridine-3-methyleneamino |
| ABC-11 | p-fluorophenyl | N-morpholinyl |
| ABC-12 | p-methoxyphenyl | N-morpholinyl |
| ABC-13 | m-methylphenyl | N-morpholinyl |
| ABC-14 | o-methoxyphenyl | N-morpholinyl |
| ABC-15 | 2,5-dimethoxyphenyl | 6-chloro-pyridine-3-methyleneamino |
| ABC-16 | 2,5-dimethoxyphenyl | N-morpholinyl |
| ABC-17 | meta-trifluoromethylphenyl | 6-chloro-pyridine-3-methyleneamino |
| ABC-18 | meta-trifluoromethylphenyl | N-morpholinyl |
| ABC-19 | 2,5-dimethoxyphenyl | N-methyl-1-piperazinyl |
| ABC-20 | meta-trifluoromethylphenyl | N-methyl-l-piperazinyl |
| ABC-21 | p-fluorophenyl | cyclopropylimine |
| ABC-22 | p-fluorophenyl | cyclohexylimine |
| ABC-23 | p-methoxyphenyl | cyclohexylimine |
| ABC-24 | meta-trifluoromethylphenyl | cyclohexylimine |
| ABC-26 | meta-trifluoromethylphenyl | meta-trifluoromethyl phenylenimine |
| ABC-27 | p-methoxyphenyl | cyclopropylimine |
| ABC-28 | meta-trifluoromethylphenyl | cyclopropylimine |
| ABC-31 | p-methoxyphenyl | 2-thiazolimine |
| ABC-32 | m-methylphenyl | 2-thiazolimine |
| ABC-33 | p-methoxyphenyl | meta-trifluoromethyl phenylenimine |
| ABC-34 | meta-trifluoromethylphenyl | 2-thiazolimine |
| ABC-39 | m-chlorophenyl | N-morpholinyl |
| ABC-40 | 3,4-dichlorophenyl | N-morpholinyl |
| ABC-41 | m-chlorophenyl | N-methyl-1-piperazinyl |
| ABC-42 | 3,4-dichlorophenyl | N-methyl-1-piperazinyl |
| ABC-43 | m-chlorophenyl | cyclopropylimine |
| ABC-44 | 3,4-dichlorophenyl | cyclopropylimine |
| ABC-45 | m-chlorophenyl | 2-thiazolimine |
| ABC-46 | 3,4-dichlorophenyl | 2-thiazolimine |
| ABC-50 | o-methoxyphenyl | 2-thiazolimine. |

3. The naphthalene diamide compound of claim 1 wherein —X—N($R_1$)($R_2$) is in the 2 position on the naphthalene ring and N($R_3$)Y—$R_4$ is in the 6 position, or X—N($R_1$)($R_2$) is in the 3 position on the naphthalene ring and —N($R_3$)—Y—$R_4$ is in the 7 position.

4. A pharmaceutical composition comprising a compound of claim 1 as an active ingredient.

5. A pharmaceutical composition comprising a compound of claim 2 as an active ingredient.

6. A pharmaceutical composition comprising a compound of claim 3 as an active ingredient.

* * * * *